United States Patent [19]

Conklin et al.

[11] Patent Number: 4,738,866
[45] Date of Patent: Apr. 19, 1988

[54] APPARATUS AND METHOD FOR DETERMINING WHETHER AN ADEQUATE AMOUNT OF SIZING HAS BEEN APPLIED TO YARN ENDS

[75] Inventors: Delano M. Conklin, Burlington; Robert H. Best, Greensboro, both of N.C.

[73] Assignee: Burlington Industries, Inc., Greensboro, N.C.

[21] Appl. No.: 28,561

[22] Filed: Mar. 20, 1987

[51] Int. Cl.$^4$ .............................................. B05C 11/00
[52] U.S. Cl. ....................................... 427/10; 118/712
[58] Field of Search ............................ 118/712; 427/10

[56] References Cited

U.S. PATENT DOCUMENTS

| | | | |
|---|---|---|---|
| 1,815,915 | 7/1931 | Kallander. | |
| 2,797,171 | 6/1957 | Fralish | 117/7 |
| 2,810,663 | 10/1957 | Reynolds et al. | 117/217 |
| 3,142,831 | 7/1964 | Horne et al. | 340/259 |
| 3,158,852 | 11/1964 | Schacher | 340/259 |
| 3,801,349 | 4/1974 | Wilson et al. | 117/31 |
| 4,024,291 | 5/1977 | Wilmanns | 427/10 |
| 4,189,335 | 2/1980 | Evans et al. | 427/10 X |

Primary Examiner—Michael R. Lusignan
Attorney, Agent, or Firm—Cushman, Darby & Cushman

[57] ABSTRACT

An automatic method and apparatus for determining whether adequate size has been applied to yarn ends includes at least one photo-optic detector for counting the number of frays or hairs at various locations of a warp beam made up of yarn ends, comparing the count to a predetermined upper limit of acceptable frays or hairs and displaying the result. An alarm is enabled whenever the detected amount of frays of hairs exceeds the predetermined acceptable upper limit. A feedback control loop provides for the control of yarn transport speed, pressure roll force and/or size pump speed to maintain the amount of applied size within an acceptable range of values.

28 Claims, 3 Drawing Sheets

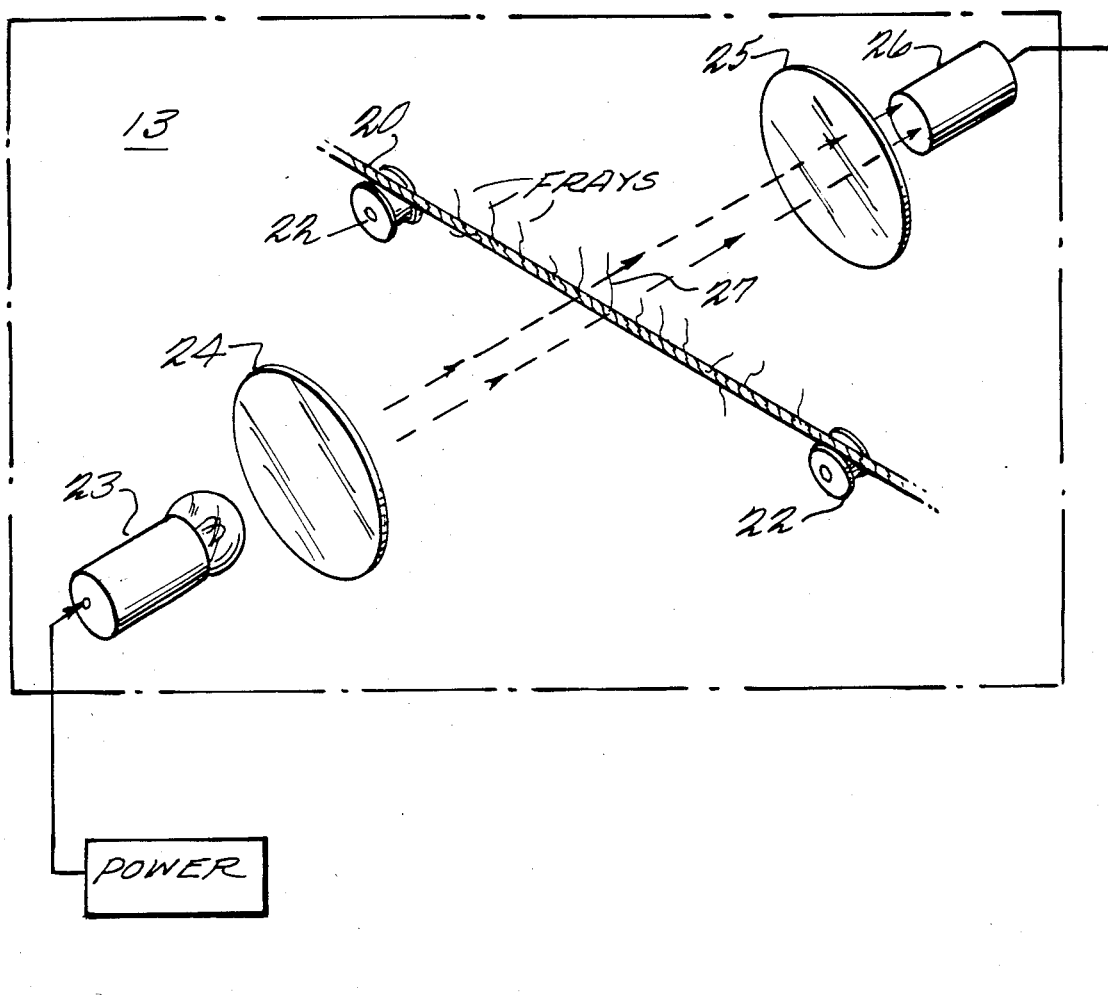
FIG. 2
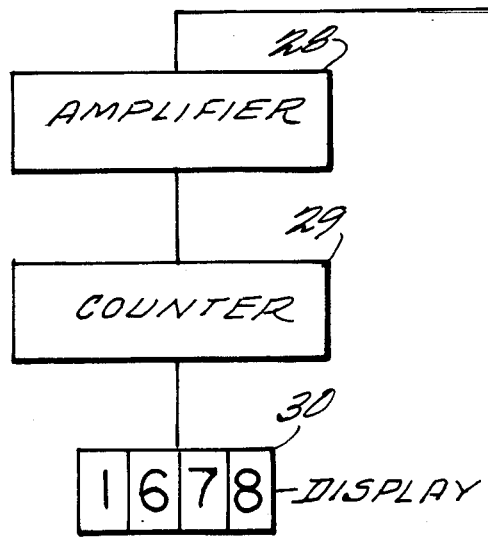

APPARATUS AND METHOD FOR DETERMINING WHETHER AN ADEQUATE AMOUNT OF SIZING HAS BEEN APPLIED TO YARN ENDS

FIELD OF THE INVENTION

The invention is directed to a method and apparatus for automatically measuring and controlling the amount of size applied to yarn ends which make up a warp beam and for providing an alarm whenever the amount of applied size is inadequate.

BACKGROUND OF THE INVENTION

In the sizing of yarn ends for weaving, it is essential that all of the thousands of ends which make up a warp beam are adequately coated with size. Sizing the ends causes the many hairs or frays that are standing out from the body of the yarn to be made to lie down against the body. This action strengthens the yarn and tends to prevent the frays from catching in the weaving process, and thus causing warp breaks. Thus, whenever an inadequate amount of sizing has been applied to the yarns making up a warp beam, production delays result during the weaving process thereby causing inefficiencies and production down time.

SUMMARY OF THE INVENTION

The present invention provides a method and apparatus for automatically determining whether or not the correct amount of size has been applied to yarn ends. The invention determines the amount of hairs or frays present at various points along a warp beam and compares this number with a predetermined number which has been manually set into the system. The predetermined number represents an upper limit of frays or hairs which is acceptable. More particularly, the predetermined number is set as the threshold above which an unacceptable amount of warp breaks will occur during the weaving process. If the detected number of hairs or frays exceeds the predetermined number then the invention determines that an improper amount of size has been applied to the warp ends. Accordingly, the invention provides an alarm which enables corrective action to take place whenever the detected number of hairs or frays exceeds the predetermined upper limit. In addition, in a preferred embodiment of the invention, the fray hair detection signal is used as a feedback control signal to adjust or control the amount of sizing applied to the yarn ends. The control is accomplished, for example by controlling the transport speed of the yarn ends, the nip roll pressure or the amount of or cencentration of sizing in the bath, in accordance with the fray hair detection signal.

BRIEF DESCRIPTION OF THE DRAWINGS

FIG. 2 is a schematic diagram of the detector shown in FIG. 1.

DETAILED DESCRIPTION OF THE INVENTION

Figure 1:
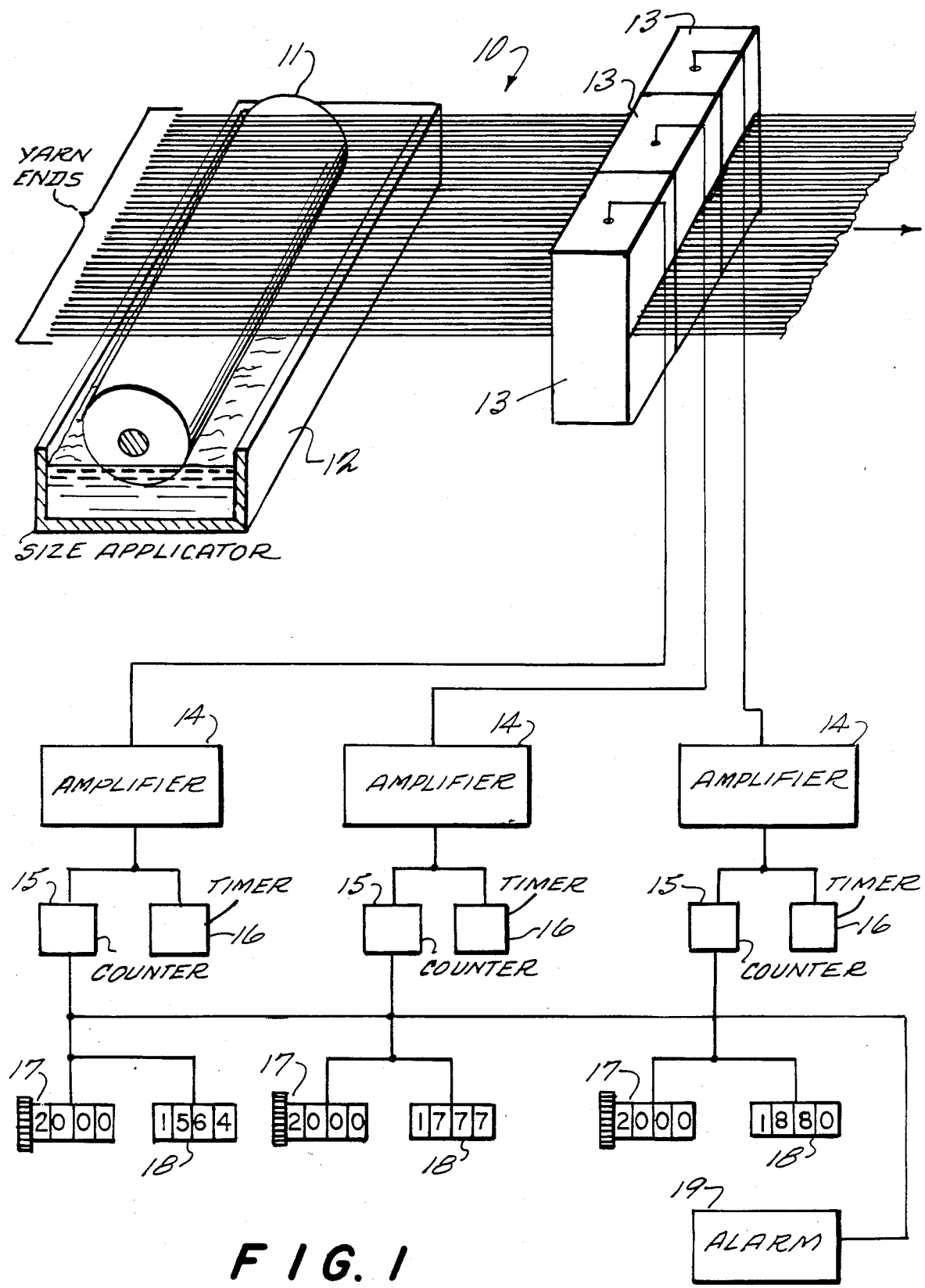
FIG. 1 is a schematic diagram of a portion of an exemplary embodiment of the present invention.

FIG. 1 shows a portion of a first exemplary embodiment of the invention to include yarn ends 10 which travel through a grooved roll 11 which is rotating in a size bath 12. The rotating action serves to apply size to each yarn end, thus causing the frays to lie down and adhere to the body of the yarn. Should the grooved roll 11 or size bath 12 fail to provide size properly (i.e., insufficient or no size applied) to the yarn ends 10 or should a condition exist which would cause insufficient size to be applied to one side of the warp beam, made up by yarn ends 10, and not the other side then it becomes important that operators be alerted immediately. Accordingly, fray detectors 13 are placed at 3 points on the warp beam, namely, right side-center-left side. The fray detectors can for example be comprised of the photo-optic detector portion (see reference numeral 13 in FIG. 2) of a Toray Fray Counter, Model DT-104. It should here be noted that the selection of 3 fray detectors represents a preferred embodiment, but as would be recognized by those skilled in the art, more or less fray detectors could also be used. The detectors 13, as will be described in greater detail hereafter, determine the fray count at each of the aforementioned three points. The detectors' output signals are amplified in amplifiers 14, which can be for example a typical small signal amplifier. After amplification and conditioning, the output is then fed to a digital counter 15, for example Omron Model H7A-4D, and an electronic timer 16, for example Omron Model H5A-4D. An acceptable fray count is predetermined and set for each of the corresponding counters via thumb wheel switches 17, which are for example an integral part of the Omron counter, Model H7A-4D. The count for this example is shown in FIG. 1 to be 2,000.

In operation, frays on the yarn at the right side-center-left side of a warp beam, which has had sizing applied, are automatically counted for a selected period of time and the counts are then compared with the count predetermined by the thumb wheel switches 17. As long as the size is being properly applied to the yarn ends, the fray count will be below the established acceptable maximum number which has been set by thumb wheel switches 17 for the given period of time. The actual count will be continuously displayed, reset, and displayed on digital display 18, which for example is also an integral part of the Omron Counter H7A-4D. Accordingly, in FIG. 1, since each of digital displays 18 shows a number less than the predetermined set number of 2,000, then it is clear that in this case adequate size has been applied to the yarn ends in order to limit the number of frays or hairs. If, however, any of the detectors should register a higher count than acceptable, i.e., a count greater than 2,000, this would be an indication that insufficient size is being applied at the particular location corresponding to the location of fray detector 13. Alarm 19 can be for example a relay, Guardian Series 1315, the output of which may be used to activate any type of external alarm, horn, light, etc. When this condition occurs, an alarm signal is sent from the counter which has counted in excess of the predetermined count number to the alarm 19.

The detector 13 is shown in greater detail in FIG. 2, which shows in schematic form a Toray Fray Counter, Model DT-104. As can be seen in FIG. 2, a yarn 20 passes through a photo-optic detector system which is comprised of a set of guides 22, light source assembly 23, magnifying lenses 24 and 25, and photo-electric converter 26, all of which comprise detectors 13. Accordingly, individual frays 27 are projected on to the converter where the optical signal is converted to an electronic signal, which is then fed to amplifier 28, counter 29 and display 30.

Figure 3:
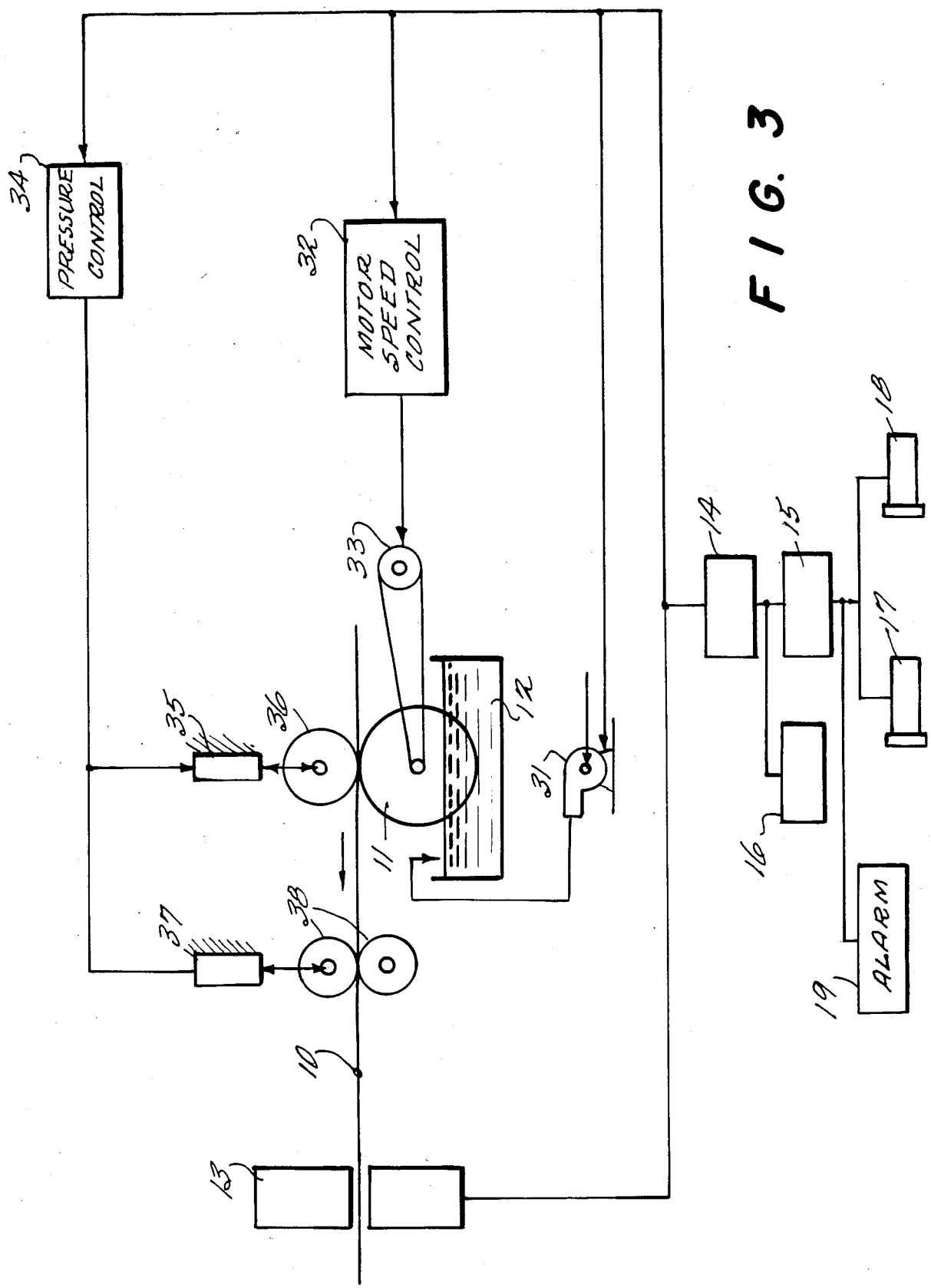
FIG. 3 is a schematic diagram of an exemplary embodiment of the present invention.

FIG. 3 shows the invention to include a feedback control system for adjusting the amount of sizing applied to the yarn ends in accordance with the output signals from detectors 13. For ease of illustration, the invention has been depicted with a single detector 13, however, as will be appreciated by those skilled in the art two or more detectors can be used, as has been shown in FIG. 1. In addition, similar components to those shown in FIGS. 1 and 2 have been given the same reference numerals and their detailed operation having already been described above have been omitted here.

The output signal from detector 13 in addition to being provided to amplifier 14, as previously shown in FIG. 1, is provided to one or more control circuits. The first control circuit comprises size pump 31 for increasing the amount of or concentration of size held within size bath 12. Thus, the speed and activation of the pump is determined by the level of the output signal from detector 13. For example, an output signal indicative of a large fray count and thus representative of an inadequate amount of sizing being applied would activate size pump 31 at a predetermined speed to replenish the amount of or concentration of sizing within size bath 12. Conversely an output signal indicative of a small fray count would inactivate size pump 31. Of course output signals indicative of fray counts ranging between a small and a large fray count would activate size pump 31 at a speed proportionally lower than the predetermined speed established for the large fray count.

The second control circuit comprises motor speed control circuit 32, drive motor 33 and grooved roll 11, which are all interconnected for transporting the yarn ends at variable speeds. As the transporting speed is increased the amount of size applied to the yarn ends is decreased. Conversely if the transporting speed is decreased the amount of size applied to the yarn ends is increased. Accordingly, if an output signal from detector 13 is indicative of a large fray count, thereby representing an inadequate amount of sizing being applied, then motor speed control circuit 32 converts the output signal to a motor drive signal which drives drive motor 33 at a reduced speed to reduce the rotational speed of grooved roll 11, thereby increasing the amount of size applied to the yarn ends. On the other hand, an output signal from detector 13, indicative of a small fray count, will be converted by motor speed control circuit 32 to a motor drive signal for driving drive motor 33 at a higher speed to increase the rotational speed of grooved roll 11, thereby decreasing the amount of size applied to the yarn ends. In this way, efficient operation can be achieved while ensuring that an adequate amount of size is applied at all times to the yarn ends. More particularly, this control scheme allows the yarn ends to be transported at the maximum speeds at which adequate sizing is applied, in order to maximize output.

The third control circuit comprises pressure control circuit 34, pressure pumps 35 and 37, nip roll 36 and pressure rolls 38. Pressure pump 35 adjusts the pressure at which nip roll 36 is driven against grooved roll 11 and pressure pump 37 adjusts the pressure at which the pair of pressure rolls 38 abut against each other. The pressure rolls 38 can be provided for squeezing excess sizing from the yarn ends. The pressure pumps 35 and 37 are driven by pressure control circuit 34 in accordance with the output signal from detector 13. More particularly, an output signal indicative of a large fray count will be converted to a pressure control signal, by pressure control circuit 34, which causes pressure pumps 35 and 37 to decrease the pressure on nip roll 36 and pressure rolls 38, respectively. In this manner corrective action is taken for a larger amount of sizing to be applied to the yarn ends. On the other hand, an output signal indicative of a small fray count will cause pressure pumps 35 and 37 to increase the pressure on their respective rolls, thereby decreasing the amount of sizing applied to the yarn ends. Pressure control circuit 34 can comprise a conventional transducer and pressure pumps 35 and 37 can be for example conventional strain gauge converters or piezoelectric actuators.

It should be appreciated that the above described description of the preferred embodiment does not limit the scope of the present invention in any way, and that various modifications can be made without departing from the spirit and scope of the present invention. For example, while the invention has been described primarily for the detection of size applied to yarn ends used in weaving, it in no way should be construed that the invention can not be used for other textile materials. For example, it is contemplated that the invention could be well used in other types of sizing applications, such as in the sizing of fiber glass yarn. Further, although one output signal from a single detector 13 has been shown for driving the control circuits, two or more detector output signals could be paralleled or the maximum or minimum signal from plural detectors could be selected as the control signal, as will be appreciated by those skilled in the art.

What is claimed is:

1. A device for determining an amount of sizing applied to a plurality of yarn ends, said device comprising:
   means for applying sizing to a plurality of yarn ends;
   detecting means, receiving said plurality of yarn ends transported from said applying means, for determining along at least two transport positions of said plurality of yarn ends the amount of sizing applied over a set period of time and for outputting at least two signals representative of the amount of sizing applied to said yarn ends, over the set period of time, at said at least two transport positions, respectively;
   display means for displaying said at least two output signals received from said detecting means; and
   alarm means for outputting an alarm whenever the amount of sizing applied at any of said two transport positions is less than a predetermined amount.

2. The device as in claim 1 said detecting means including at each of said at least two transport positions:
   means for determining an amount of frays on at least one yarn end and for outputting a fray signal representative of said determined amount;
   timer means for measuring the set period of time and outputting a timer signal at the end of the set period of time; and
   counting means for receiving said fray signal from said determining means and said timer signal from said timer means and for outputting a signal representative of the amount of sizing applied to said yarn end, in accordance with the received signals, to said display means.

3. The device as in claim 1, said yarn ends being made of material for weaving cloth.

4. An apparatus for determining the amount of sizing applied to a plurality of yarn ends comprising:
   means for moving said yarn ends at a selectable speed;

detecting means for measuring the fray count of said yarn ends and providing a count value representative thereof, said count value being inversely proportional to the amount of sizing applied to said yarn ends, said detecting means including a fray detector; a timer for measuring an interval of time; and counting means connected to said fray detector and said timer for generating the count value as the fray count detected during said time interval.

5. The apparatus as in claim 4 further including display means connected to said detecting means for displaying said count value.

6. The apparatus as in claim 4 further including comparison means for receiving said count value, comparing said count value to a predetermined value corresponding to the acceptable amount of sizing applied to said yarn ends and providing an output signal representative of said count value.

7. The apparatus as in claim 6 further including alarm means connected to said comparison means for outputting an alarm in response to said output signal exceeding said predetermined value.

8. The apparatus as in claim 6 further including setpoint means connected to said comparison means for setting said predetermined value.

9. A yarn slashing apparatus comprising:
means for applying sizing to yarns in an adjustable quantity;
means for moving said yarn ends at a selectable speed;
detecting means for measuring the fray count of said yarn ends and providing a count value representative thereof, said count value being inversely proportional to the amount of sizing applied to said yarn ends, said detecting means including a fray detector; a timer for measuring an interval of time; and counting means connected to said fray detector and said timer tor generating the count value as the fray count detected during said time interval; and
control means for adjusting said sizing applying means to compensate for out-of-range sizing amounts detected by said detecting means.

10. The yarn slashing apparatus as in claim 9 wherein the sizing applying means includes a size box with exit nip rolls, the pressure of the exit nip rolls being adjustable to vary the sizing quantity and the control means adjusting the pressure of the exit nip rolls in accordance with the output signal from said detecting means.

11. The yarn slashing apparatus as in claim 9 wherein the sizing applying means includes a size box and means for providing a variable concentration size formulation therein, said control means adjusting the size formulation concentration in accordance with the output signal from said detecting means.

12. The yarn slashing apparatus as in claim 9 further comprising creel means for supplying the yarns to a size box and beaming means for taking up the sized yarns.

13. The yarn slashing apparatus as in claim 11 further comprising sizing formulation tanks and communication means from said sizing formulation tanks to the size box, said control means being operatively associated with said communication means.

14. The yarn slashing apparatus as in claim 9, said control means controlling said yarn moving means to move said yarns at any one of a plurality of selectable speeds, wherein said control means increases the speed of said moving means when said detecting means detects a low fray count and decreases the speed of said moving means when said detecting means detects a high fray count.

15. The yarn slashing apparatus as in claim 9 wherein the sizing applying means includes a size box with yarn transporting rolls, the pressure of the yarn transporting rolls being adjustable to vary the sizing quantity and the control means adjusting the pressure of the transporting rolls in accordance with the output signal from said detecting means.

16. A method for determining an amount of sizing applied to a plurality of yarn ends, said method comprising the steps of:
applying sizing to a plurality of yarn ends;
determining along at least two transport positions of said plurality of yarn ends the amount of sizing applied over a set period of time
outputting the determined amount of sizing applied to said yarn ends, over the set period of time, for each of said at least two transport positions, respectively;
displaying the at least two determined amounts of sizing; and
generating an alarm whenever the amount of sizing applied at any of said two transport positions is less than a predetermined amount.

17. The method as claimed in claim 16, wherein the determining step includes:
detecting an amount of frays on at least one yarn end and outputting a fray signal representative of said detected amount;
measuring the set period of time and outputting a timer signal at the end of the set period of time; and
comparing said fray signal and said timer signal and producing a signal representative of the amount of sizing applied to said yarn end.

18. A method of determining the amount of sizing applied to a plurality of yarn ends comprising:
detecting frays in a length of yarn;
measuring the length of yarn in which the frays were detected; and
generating the count value as the fray count detected along the length.

19. The method as recited in claim 18 wherein said length measuring step includes measuring the speed of yarn passing a fixed point in a known time interval.

20. The method as recited in claim 18 further including displaying said count value.

21. The method as recited in claim 18 further including comparing said count value to a predetermined value corresponding to the acceptable amount of sizing applied to said yarn ends and providing a output signal when said count value varies from said predetermined value.

22. The method as recited in claim 21 further including outputting an alarm in response to said output signal.

23. The method as recited in claim 21 further including providing said predetermined value.

24. A method of yarn slashing comprising the steps of:
applying sizing to yarns in an adjustable quantity;
determining the amount of sizing applied to the yarns by measuring the fray count of said yarn ends to provide a count value representative thereof, said count value being proportional to the amount of sizing applied to said yarn ends; and adjusting the quantity of sizing applied to the yarns to compensate for out-of-range sizing amounts detected in said determining step.

25. The method of yarn slashing as in claim 24 wherein the sizing applying step includes nipping the yarns as they exit from a size box with exit nip rolls which are pressure adjustable to vary the sizing quantity applied to the yarns and the adjusting step adjusts the nip rolls.

26. The method of yarn slashing as in claim 24 wherein the sizing applying step includes passing the yarn through a size formulation the concentration of which is variable and the adjusting step adjusts the size formulation concentration.

27. The method of yarn slashing as in claim 24 further comprising supplying the yarns to a size box from a slasher creel and taking up the sized yarns on a beamer.

28. The method of yarn slashing as in claim 24, wherein said adjusting step includes adjusting the transport speed of the yarns.

* * * * *